United States Patent [19]

Albano et al.

[11] Patent Number: 5,266,267

[45] Date of Patent: Nov. 30, 1993

[54] INCUBATOR WITH NON-SPOTTING EVAPORATION CAPS

[75] Inventors: Thomas Albano, Churchville; William R. Kelly, Seneca Falls, both of N.Y.

[73] Assignee: Eastman Kodak Company, Rochester, N.Y.

[21] Appl. No.: 23,331

[22] Filed: Feb. 26, 1993

[51] Int. Cl.$^5$ .............................................. G01N 21/00
[52] U.S. Cl. ....................................... 422/64; 422/63; 436/46
[58] Field of Search ............... 422/63, 64, 67; 436/43, 436/46

[56] References Cited

U.S. PATENT DOCUMENTS 5,034,191  7/1991  Porte ..................................... 436/46

5,037,613  8/1991  Shaw et al. ............................ 422/64

Primary Examiner—James C. Housel
Assistant Examiner—Lien Tran
Attorney, Agent, or Firm—Dana M. Schmidt

[57] ABSTRACT

A method and apparatus for preventing spotting of the undersurface of the evaporation caps of an incubator in a clinical analyzer. It has been discovered that the surprising cause of the problem was electrostatic attraction building up on the caps, due to the use of plastic parts. The solution to that problem is the provision, in a plastic cover plate mounting the incubator housing on its drive spindle, with carbon fibers rather than glass fibers, in an amount sufficient to provide a volume resistivity throughout the plastic of between about $10^5$ and about $10^9$ ohm-cm, and grounding the housing through the spindle on which it is mounted.

6 Claims, 2 Drawing Sheets

INCUBATOR WITH NON-SPOTTING EVAPORATION CAPS

FIELD OF THE INVENTION

The invention relates to incubators and incubation methods used in an analyzer, especially those incubators that use plastic parts, such as for the rotor.

BACKGROUND OF THE INVENTION

It has been common for incubators, such as are used in the "Ektachem" TM brand of clinical analyzers manufactured by Eastman Kodak Co. since 1982, to use plastic evaporation caps that cover plastic slides after the latter are slid into place under the caps, for incubation. During the use of thousands of such incubators, over the years, there has never been a problem, until recently, of the sample liquid that is predeposited onto the slides, spotting also the under-surface of the evaporation cap positioned above it.

However, recent modifications in the design have recently caused, in some instances, such spotting to occur. Some of those modifications include coating the incubator rotor disk with "Marten Hardcoat", a ceramic/"Teflon" TM based material, to reduce wear and carry-over of ammonia from ammonia-producing slides, and converting portions of the housing of the incubator from metal to glass-filled plastic, for savings in cost and weight. The latter change has featured plastic connecting members that mount the rotating incubator to a drive spindle. The spotting is highly objectionable because of the color shift in the white reflectance of the evaporation cap, a problem particularly when using translucent slide elements.

The obvious cause of the problem was thought to be one of inertia. The caps must be snapping down too hard onto the captured slide so as to cause residual liquid not yet absorbed by the slide, to "jump up". The solutions that were tried for this problem were: a) to prevent such snapping action by the cap, and/or b) to double the height of the cap under-surface above the slide to prevent the inertially-displaced liquid from reaching it. However, none of these solutions was found to be effective. In fact, we have surprisingly discovered that inertia is not the cause of the problem at all.

Hence, prior to this invention, there has been an unsolved problem of sample liquid deposited on plastic, liquid-absorbing slide test elements, also becoming deposited in small amounts on the undersurface of the evaporation cap disposed above the slide element when the latter is in an incubator.

SUMMARY OF THE INVENTION

We have discovered that the real, and surprising, cause of the problem is electrostatic charge build-up in the evaporation caps, causing liquid to "jump" off the slide test element, notwithstanding the liquid-absorbing nature of the test element.

To deal with this surprising cause, the invention comprises, in accordance with one aspect thereof, a method for preventing spotting with sample liquid of an evaporation cap above a slide test element in an incubator, the incubator comprising: an electrically grounded drive spindle and means for rotating it, a housing mounted on the drive spindle and having stations for supporting slide test elements in the incubator, the stations each including a slide element support surface and a movable evaporation cap above the surface, the housing also comprising connector members, physically mounted on the drive spindle, at least the connector members being formed of a plastic material to minimize cost and weight. The method comprises adding to the plastic material when manufacturing at least the connector members, enough carbon fibers to provide a volume resistivity throughout the plastic material of between about $10^5$ and $10^9$ ohm-cm, and electrically grounding the connector members to the drive spindle.

In accordance with another aspect of the invention, there is provided an incubator for a clinical analyzer, the incubator comprising: an electrically grounded drive spindle and means for rotating it, a housing mounted on the drive spindle and having stations for supporting slide test elements in the incubator, the stations each including a slide element support surface and a movable evaporation cap above the support surface, the housing also comprising connector members electrically and physically connected to the drive spindle, at least the connector members being formed of a plastic material to minimize cost and weight. The incubator is improved in that the plastic material includes enough carbon fibers to provide a volume resistivity throughout the plastic material of between about $10^5$ and $10^9$ ohm-cm, such that any electrostatic charges generated in the stations will be grounded through the drive spindle.

In accordance with yet another aspect of the invention, there is provided a clinical analyzer comprising a source of patient sample liquid, a source of slide test elements, a dispensing station for transferring a patient liquid to a slide test element, an incubator, and a detection station, the improvement wherein the incubator further comprises all of the features noted in the previous paragraph.

Therefore, it is an advantageous feature of the invention that unwanted spotting of sample liquid onto the evaporation cap is drastically reduced, without sacrificing the advantage of using plastic as at least part of the incubator housing.

Other advantageous features will become apparent upon reference to the following detailed description, when read in light of the attached drawings.

DETAILED DESCRIPTION OF PREFERRED EMBODIMENTS

The following description sets forth the invention in its preferred use, wherein a portion of the incubator housing is formed from polycarbonate plastic, another portion is of metal, and certain preferred analyzer parts are associated with the incubator. Also, a preferred type of evaporation cap and spring are disclosed. In addition, the invention is useful regardless of whether the incubator housing is all plastic, or only the part connected to the drive spindle is plastic, and regardless of the type of plastic. It is further useful regardless of the type of cap or spring that are used, although it is most applicable when using plastic evaporation caps. Still further, the invention is independent of the kinds of stations used to supply patient samples, slide elements, or provide detection.

Figure 1:
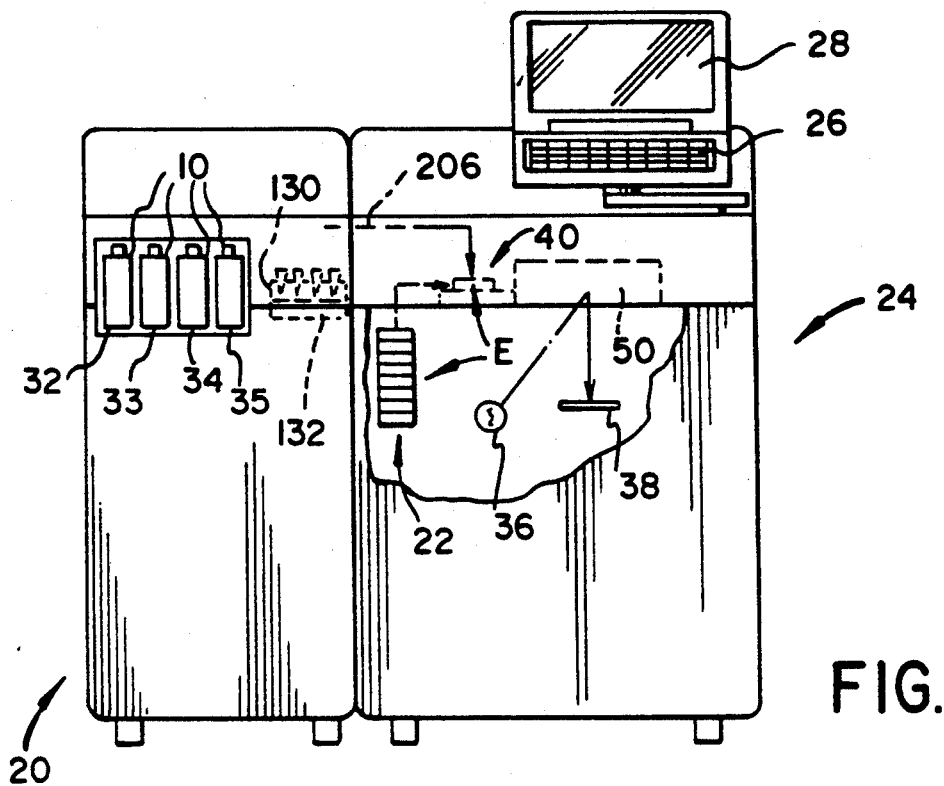
FIG. 1 is a partially schematic, partially broken-away elevational view of an analyzer using the invention.

As shown in FIG. 1, an analyzer using the invention conventionally includes a source of patient sample, shown as station 20, which supplies trays 10 on tracks 31-35, each tray holding a plurality of patient serum tubes. These trays are each moved into an aspirating and dispensing device 206 that moves from station 20, to the other portion 24 of the analyzer that provides slide test elements E (station 22), incubator 50 and detector 36, 38. Sample is dispensed at station 40 onto an element E. Input/output devices 26 and 28 are also provided. All of this is conventional, having been described, for example, in U.S. Pat. Nos. 5,008,082 (for station 20) and 5,089,418 (for station 24).

Figure 2:
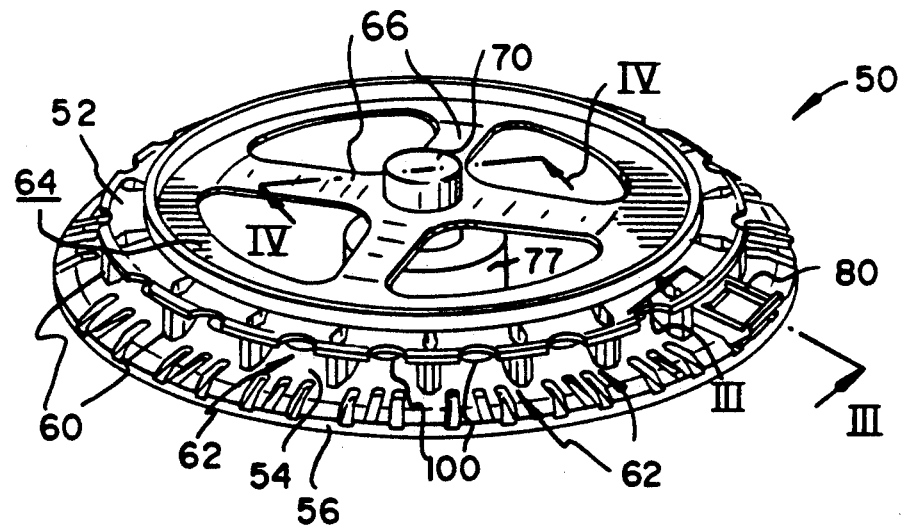
FIG. 2 is an isometric view of most of the incubator of the analyzer of FIG. 1, showing especially the incubator housing, and only one evaporation cap.

Incubator 50, FIG. 2, comprises, as is conventional, a housing 52 which in turn includes a slide test element support surface 54 provided by bottom plate 56, side walls 60 dividing up surface 54 into a plurality of test element stations 62. Upper plate 64 closes off each station 62, and preferably a plurality, e.g., four connector members 66 extend from plate 64 to a central orifice that is mounted around a drive spindle 70. Spindle 70 in turn is driven by motor 77, which is grounded to a hot plate 112, FIG. 4. At every station 62, an evaporation cap and spring, described below, are provided, although only one is shown in FIG. 2.

Figure 3:
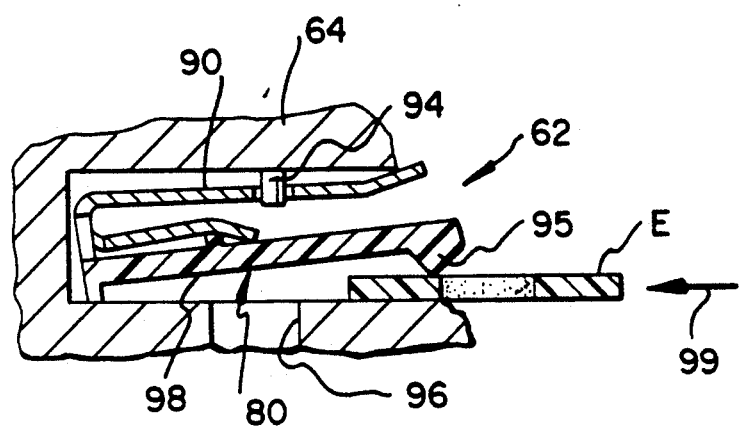
FIG. 3 is a fragmentary elevational view taken in section generally along the line III—III of FIG. 2.

Evaporation cap 80, FIG. 3, is spring-biased downwardly at each station 62 by a spring 90, shaped in the form of a "J" and held there by a pin 94 depending from upper plate 64. The features shown in FIG. 3 are more clearly explained in, e.g., U.S. Pat. No. 5,106,586. Camming feet 95 allow the cap to clear the slide element E as that is pushed in, arrow 99. Aperture 96 is used to scan element E using the beam emanating from light source 36, FIG. 1.

All of the above incubator features and their functions are conventional. They can be further understood, for example, by reference to the incubator in the analyzer available under the trademark "Ektachem 250" from Eastman Kodak Co.

Under-surface 98 of cap 80 is the surface that, prior to this invention, was evidencing "spotting" of sample. It was first thought this was due to the snap-down of the cap caused by spring 90, when camming feet 95 clear the slide element E being pushed in.

At least connector members 66 preferably comprise a plastic material. Housing 52 is most preferably plastic in all parts except plate 56 and spring 90, which are metal. Most preferably, the plastic material comprises polycarbonate, such as is available under the brand name "Lexan" TM from G.E. Co.

In the past, this polycarbonate has been filled with glass fibers for additional strength. In accordance with this invention, the glass fibers are replaced with carbon fibers in an amount sufficient to provide the electrical conductivity needed to bleed off to ground any electrostatic charges that might otherwise accumulate. This amount will of course vary, depending on the innate conductivity of the plastic used and the loading ratio of the carbon fibers. The amount is selected to provide a volume resistivity throughout the plastic that is between about $10^5$ and $10^9$ ohm-cm. Above about $10^9$ ohm-cm, there is insufficient conductivity to bleed off the charges in a reasonable length of time. Below about $10^5$ ohm-cm, the mass of carbon fibers becomes so large as to interfere with the plastic molding process, and no improvement in bleeding off the charges can be noticed by the addition of more carbon fibers. When used with polycarbonate, a preferred amount of carbon fibers is about 10% by weight.

Any carbon fibers can be used. One example is fibers that are about 0.6 cm long and 7 to 10 microns in diameter, e.g., those available already in polycarbonate at a 10% weight ratio, under the trade name "Electro-fill" J50/CF/10/DP from DSM Co.

Figure 4:
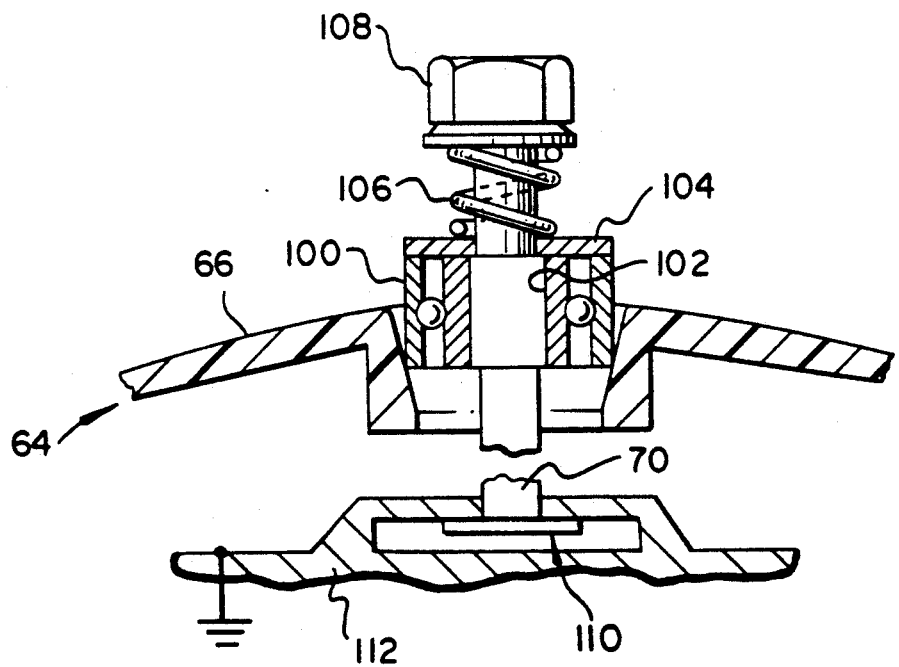
FIG. 4 is a fragmentary elevational view taken in section generally along the line IV—IV of FIG. 2, to illustrate the connection of the incubator housing to the drive spindle.

The bleeding off of plate 64 is via its electrical connection to drive spindle 70, shown in greater detail, FIG. 4. That is, plate 64 has its connector members 66 connected to a metal rotor bearing 100, the inner cylinder 102 of which is attached to spindle 70. Bearing 100 and plate 64 are pressed downward via a washer 104 and compressive spring 106 secured by nut 108 on the top of spindle 70. The opposite, bottom end 110 of spindle 70 is in rotating contact with hot plate 112 (the drive motor of the spindle not being shown in FIG. 4.) Since plate 112 is grounded, the electrostatic charges, if any, in the incubator are thus bled off via the conductivity of plastic connector members 66, to spindle 70 and thence to ground.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention as set forth in the claims.

What is claimed is:

1. A method for preventing spotting with sample liquid of an evaporation cap above a slide test element in an incubator, the incubator further comprising: an electrically grounded drive spindle and means for rotating said drive spindle, a housing mounted on said drive spindle and having stations for supporting slide test elements in the incubator, said stations each including a slide element support surface and a movable evaporation cap above said surface, said housing also comprising connector members, physically mounted on said drive spindle, at least said connector members being formed of a plastic material to minimize cost and weight;

the method comprising adding to said plastic material when manufacturing at least said connector members, enough carbon fibers to provide a volume resistivity throughout said plastic material of between about $10^5$ and $10^9$ ohm-cm, and electrically grounding each of said stations through said connector members to said drive spindle.

2. A method as defined in claim 1, wherein said plastic material comprises polycarbonate.

3. In an incubator for a clinical analyzer, the incubator comprising: an electrically grounded drive spindle and means for rotating said drive spindle, a housing mounted on said drive spindle and having stations for supporting slide test elements in the incubator, said stations each including a slide element support surface and a movable evaporation above said surface, said housing also comprising connector members electrically and physically connected to said drive spindle, at least said connector members being formed of a plastic material to minimize cost and weight;

the improvement wherein said plastic material includes enough carbon fibers to provide a volume resistivity throughout said plastic material of between about $10^5$ and $10^9$ ohm-cm wherein each of said stations is electrically grounded through said connector member to said drive spindle, such that any electrostatic charges generated in said stations will be grounded through said drive spindle.

4. An incubator as defined in claim 3, wherein said plastic material comprises polycarbonate.

5. In a clinical analyzer comprising a source of patient sample liquid, a source of slide test elements, a dispensing station for transferring a patient liquid to a slide test element, an incubator, and a detection station, said incubator further comprising: an electrically grounded drive spindle and means for rotating said drive spindle, a housing mounted on said drive spindle and having stations for supporting slide test elements in the incubator, said stations each including a slide element support surface and a movable evaporation above said surface, said housing also comprising connector members electrically and physically mounted on said drive spindle, at least said connector members being formed of a plastic material to minimize cost and weight;

the improvement wherein said plastic material includes enough carbon fibers to provide a volume resistivity throughout said plastic material of between about $10^5$ and $10^9$ ohm-cm wherein each of said stations is electrically grounded through said connector member to said drive spindle, such that any electrostatic charges generated in said stations will be grounded through said drive spindle.

6. An analyzer as defined in claim 5, wherein said plastic material comprises polycarbonate.

* * * * *

UNITED STATES PATENT AND TRADEMARK OFFICE
CERTIFICATE OF CORRECTION

PATENT NO.  : 5,266,267
DATED       : November 30, 1993
INVENTOR(S) : Thomas Albano and William R. Kelly It is certified that error appears in the above-identified patent and that said Letters Patent is hereby corrected as shown below:

Column 4, line 66 should read:   --and a movable evaporation cap above said surface, said--

Column 6, line 3 should read:    --surface and a movable evaporation cap above said surface,--

Signed and Sealed this

Thirteenth Day of June, 1995

Attest:

BRUCE LEHMAN

Attesting Officer

Commissioner of Patents and Trademarks